US005846976A

United States Patent [19]
Batchelor et al.

[11] Patent Number: 5,846,976
[45] Date of Patent: Dec. 8, 1998

[54] ANDROSTENONE DERIVATIVE

[75] Inventors: Kenneth William Batchelor, Chapel Hill; Stephen Vernon Frye, Durham; George F. Dorsey, Jr., Raleigh; Robert A. Mook, Jr., Chapel Hill, all of N.C.

[73] Assignee: Glaxo Wellcome Inc., Research Triangle Park, N.C.

[21] Appl. No.: 708,167

[22] Filed: Aug. 22, 1996

Related U.S. Application Data

[60] Division of Ser. No. 405,120, Mar. 16, 1995, Pat. No. 5,565,467, which is a continuation-in-part of PCT/US94/10530, Sep. 16, 1994, which is a continuation-in-part of Ser. No. 123,280, Sep. 17, 1993, abandoned.

[51] Int. Cl.$^6$ .................................................... A61K 31/58
[52] U.S. Cl. ............................................................ 514/284
[58] Field of Search ............................................. 514/284

[56] References Cited

U.S. PATENT DOCUMENTS

| | | |
|---|---|---|
| 4,191,759 | 3/1980 | Johnston et al. . |
| 4,220,775 | 9/1980 | Rasmusson et al. . |
| 4,317,817 | 3/1982 | Blohm et al. . |
| 4,361,578 | 11/1982 | Alig et al. . |
| 4,377,584 | 3/1983 | Rasmusson et al. . |
| 4,760,071 | 7/1988 | Rasmusson et al. . |
| 4,814,324 | 3/1989 | Borris et al. . |
| 4,882,319 | 11/1989 | Holt et al. . |
| 4,888,336 | 12/1989 | Holt et al. . |
| 4,910,226 | 3/1990 | Holt et al. . |
| 4,937,237 | 6/1990 | Holt et al. . |
| 4,954,446 | 9/1990 | Holt et al. . |

(List continued on next page.)

FOREIGN PATENT DOCUMENTS

| | | |
|---|---|---|
| 004 949 A1 | 4/1979 | European Pat. Off. . |
| 052 799 A1 | 10/1981 | European Pat. Off. . |
| 155 096 A2 | 2/1985 | European Pat. Off. . |
| 314 199 A1 | 2/1985 | European Pat. Off. . |
| 200 859 A1 | 2/1986 | European Pat. Off. . |
| 271 219 A1 | 11/1987 | European Pat. Off. . |
| 271 220 A1 | 11/1987 | European Pat. Off. . |
| 277 002 A2 | 1/1988 | European Pat. Off. . |
| 285 382 A2 | 3/1988 | European Pat. Off. . |
| 285 383 A2 | 3/1988 | European Pat. Off. . |
| 298 652 A2 | 6/1988 | European Pat. Off. . |
| 343 954 A2 | 5/1989 | European Pat. Off. . |

(List continued on next page.)

OTHER PUBLICATIONS

Ahmad, M.S. et al., "Beckmann Rearrangement of Some Steroid a–Hydroxy Ring B Ketoximes: 5–Oxo 5,6–Seco Nitriles," *Aust. J. Chem.*, 27, pp. 1537–1543, 1974.

Hsia, S.L. and Voigt, W., "Inhibition of Dihydrotestosterone Formation: An Effective Means of Blocking Androgen Action in Hamster Sebaceous Gland," *Journal of Investigative Dermatology*, 62, No. 3, pp. 224–227, 1974.

Holt, D.A., et al., "Steroidal A Ring Aryl Carboxylic Acids: A New Class of Steroid 5a–Reductase Inhibitors," *J. Med. Chem.*, 33, pp. 937–942, 1990.

Rasmusson, G.H., et al., "Azasteroids as Inhibitors of Rat Prostatic 5a–Reductase," *J. Med. Chem.*, 27, No. 12, pp. 1690–1701, 1984.

Liang, T., et al., "Biochemical and Biological Studies with 4–AZA–Steroidal 5a–Reductase Inhibitors," *J. Steroid Biochem.*, 19, No. 1, pp. 385–390, 1983D.

House, H.O., "The Alkylation of Active Methylene Compounds," *Modern Synthetic Reactions*, 2d edition, pp. 492–570, The Benjamin/Cummings Publishing Co., 1972.

Rosini, G. and Medici, A., "Cleavage of a–Hydroxy–ketoximes Under Mild Conditions Using Phosphonitrile Dichloride," *Communications*, pp. 665–666, Oct. 1975.

Hugl, H. and Zbiral, E., "Umsetzungen Von $\Delta^5$–Steroidolefinen Mit $Pb(OAc)_{4-n}(N_3)_n{}^1$," *Tetrahedron*, 29, pp. 759–767, 1973.

Lazbin, I.M. and Koser, G.F., "Direct Conversion of Aliphatic Carboxamides to Alkylammonium Tosylates with [Hydroxy(tosyloxy)iodo]benzene," *J. Org. Chem.*, 51, No. 14, pp. 2669–2671, 1986.

Zbiral, E., et al., "Transferreaktionen Mit Hilfe Von Pb–I–V–Acetat–IV$^1$," *Tetrahedron*, 26, pp. 1427–1434, 1970.

Zbiral, E. and Nestler, G., "Transferreaktionen Mit Hilfe Von Phenyl–Jodosoacetat–I$^{1*}$" *Tetrahedron*, 26, pp. 2945–2951, 1970.

Lettre, H., et al., "Verbesserung der Darstellung von 6–Aza–steroiden," *Liebigs Ann. Chem.* 703, pp. 147–151, 1967.

Fieser, L.F. and Rajagopalan, S., "Selective Oxidation with N–Bromosuccinimide," Converse Memorial Laboratory, Cambridge 38, Massachusetts, Jun. 1949.

(List continued on next page.)

*Primary Examiner*—Zohreh Fay
*Attorney, Agent, or Firm*—Robert H. Brink

[57] ABSTRACT

The present invention relates to the compound of formula (I),

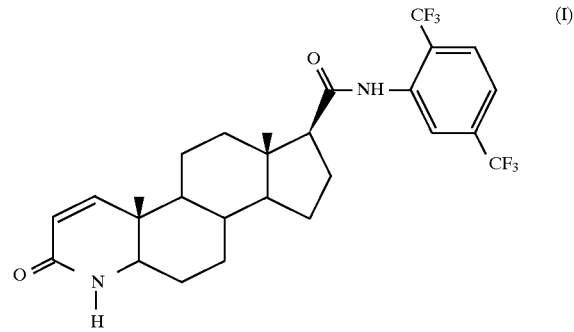

also known as 17β-N-(2,5-bis(Trifluoromethyl))phenylcarbamoyl-4-aza-5α-androst-1-en-3-one, solvates thereof, its preparation, intermediates used in its preparation, pharmaceutical formulations thereof and its use in the treatment of androgen responsive and mediated diseases.

8 Claims, No Drawings

U.S. PATENT DOCUMENTS

| | | |
|---|---|---|
| 4,966,897 | 10/1990 | Angelastro et al. ............... 514/177 |
| 4,966,898 | 10/1990 | Angelastro et al. . |
| 5,017,568 | 5/1991 | Holt et al. . |
| 5,041,433 | 8/1991 | Holt et al. . |
| 5,061,801 | 10/1991 | Williams et al. . |
| 5,061,802 | 10/1991 | Steinberg et al. . |
| 5,061,803 | 10/1991 | Williams . |
| 5,098,908 | 3/1992 | Steinberg et al. . |
| 5,110,939 | 5/1992 | Holt et al. . |
| 5,278,159 | 1/1994 | Bakashi et al. . |
| 5,318,961 | 6/1994 | Weintraub et al. . |
| 5,342,948 | 8/1994 | Panzeri et al. . |
| 5,378,710 | 1/1995 | Biollaz . |
| 5,380,728 | 1/1995 | Rasmusson . |

FOREIGN PATENT DOCUMENTS

| | | |
|---|---|---|
| 367 502 A1 | 10/1989 | European Pat. Off. . |
| 375 344 A1 | 12/1989 | European Pat. Off. . |
| 375 345 A1 | 12/1989 | European Pat. Off. . |
| 375 347 A1 | 12/1989 | European Pat. Off. . |
| 375 349 A1 | 12/1989 | European Pat. Off. . |
| 375 351 A1 | 12/1989 | European Pat. Off. . |
| 414 490 A2 | 8/1990 | European Pat. Off. . |
| 414 491 A2 | 8/1990 | European Pat. Off. . |
| 414 529 A2 | 8/1990 | European Pat. Off. . |
| 427 434 A2 | 10/1990 | European Pat. Off. . |
| 428 366 A2 | 11/1990 | European Pat. Off. . |
| 435 321 A2 | 12/1990 | European Pat. Off. . |
| 462 661 A2 | 6/1991 | European Pat. Off. . |
| 462 662 A2 | 6/1991 | European Pat. Off. . |
| 462 664 A2 | 6/1991 | European Pat. Off. . |
| 462 665 A2 | 6/1991 | European Pat. Off. . |
| 462 668 A2 | 6/1991 | European Pat. Off. . |
| 469 547 A2 | 7/1991 | European Pat. Off. . |
| 469 548 A2 | 7/1991 | European Pat. Off. . |
| 473 225 A2 | 8/1991 | European Pat. Off. . |
| 473 226 A2 | 8/1991 | European Pat. Off. . |
| 478 066 A2 | 9/1991 | European Pat. Off. . |
| 484 094 A2 | 10/1991 | European Pat. Off. . |
| 5-170789 A | 12/1991 | Japan . |
| WO 91/12261 | 8/1991 | WIPO . |
| WO 92/16213 | 10/1992 | WIPO . |
| WO 92/16233 | 10/1992 | WIPO . |
| WO 92/18132 | 10/1992 | WIPO . |
| WO93/13124 | 7/1993 | WIPO . |
| WO 93/23038 | 11/1993 | WIPO . |
| WO 93/23039 | 11/1993 | WIPO . |
| WO 93/23040 | 11/1993 | WIPO . |
| WO 93/23041 | 11/1993 | WIPO . |
| WO 93/23042 | 11/1993 | WIPO . |
| WO 93/23048 | 11/1993 | WIPO . |
| WO 93/23050 | 11/1993 | WIPO . |
| WO 93/23051 | 11/1993 | WIPO . |
| WO 93/23053 | 11/1993 | WIPO . |
| WO 93/23419 | 11/1993 | WIPO . |
| WO 93/23420 | 11/1993 | WIPO . |
| WO 94/03475 | 2/1994 | WIPO . |
| WO 94/03476 | 2/1994 | WIPO . |
| WO 94/07861 | 4/1994 | WIPO . |
| WO 94/07909 | 4/1994 | WIPO . |
| WO 94/11004 | 5/1994 | WIPO . |
| WO 94/11386 | 5/1994 | WIPO . |
| WO 94/14833 | 7/1994 | WIPO . |
| WO 95/02607 | 1/1995 | WIPO . |

OTHER PUBLICATIONS

Shoppee, C.W. and Roy, S.K., "Beckmann Rearrangement of Some a–Hydroxy–ketoximes," Dept. of Organic Chemistry, University of Sydney, Sydney, N.S.W., Australia, Dec. 1962.

Onda, M. and Takeuchi, K., "Alumina–Induced Reactions of Steroidal Oxime Acetates," *Chem. Pharm. Bull.*, 21, No. 6, pp. 1287–1290, 1973.

Staunton, J. and Eisenbraun, E.J., "3b–Acetoxzyetienic Acid," *Organic Syntheses*, pp. 8–11, 1981.

Suzuki, M., et al., "Palladium(O)–Catalyzed Reaction of a,b–Epoxy Ketones Leading to b–Diketones," *Journal of the American Chemical Society*, 102, No. 6, pp. 2095–2096, Mar. 12, 1980.

Wallis, E.S. and Lane, J.F., "The Hoffmann Reaction," *Organic Reactions*, Chapter 7,Krieger Publishing Company, Malabar, Florida, 1975.

Frye, S.V., et al., "6–Azasteroids: Potent Dual Inhibitors of Human Type 1 and 2 Steroid 5a–Reductase," *Journal of Medicinal Chemistry*, 36, No. 26, pp. 4313–4315, 1993.

Frye, S.V., et al., "6–Azasteroids; Structure–Activity Relationships for Inhibition of Type 1 and 2 Human 5a–reductase and Human Adrenal 3β–Hydroxy–$\Delta^5$–steroid Dehydrogenase/3–Keto–$\Delta^5$–steroid Isomerase," (full paper corresponding to reference CS), 1981.

Petrow, V., et al., "6–Methylene–4–Pregnen–3–Ones as Irreversible Inhibitors of Rat Prostatic $\Delta^4$–3 Ketosteroid 5a–Reductase," *Steroids*, 38, No. 2, pp. 121–140, 1981.

Robaire, B. et al., "Selective Inhibition of Rat Epididymal Steroid $\Delta^4$–5a–Reductase by Conjugated Allenic 3–Oxo–5, 10–Secosteroids," *Jrnl. of Steroid Biochemistry*, 8, pp. 307–310, 1977.

Imperato–McGinley, J. and Gautier, T., "Inherited 5a–Reductase Deficiency in Man," *TIG*, pp. 130–133, May 1986.

Brooks, J.R., et al., "5a–Reductase Inhibitory and Anti–Androgenic Activities of Some 4–Azasteroids in the Rat," *Steroids*, 47, pp. 1–19, Jan. 1986.

Brown, L., et al., "The Synthesis of Some Cholesterol Derivatives as Probes for Mechanisms of Cholesterol Metabolism," *J. Chem. Soc.*, pp. 595–599, 1987.

Rasmusson, G.H., et al., "Steroids: Structure–Activity Relationships for Inhibition of 5a–Reductase and Androgen Receptor Binding," *J. Med. Chem*, 29, pp. 2298–2315, 1986.

Stoner, E., "The Clinical Development of a 5a–Reductase Inhibitor, Finasteride," *J. Steroid Biochem. Molec. Biol.*, 37, No. 3, pp. 375–378, 1990.

van Velthuysen, J.A., et al., "Synthesis of (±)–N–Methyl–6–aza–8(14)–dehydro–19–nor–testosterone," *Tetrahedron Letters*, 27, pp. 3081–3086, 1966.

Bhattacharya, A., et al., "Acylimidazolides as Versatile Synthetic Intermediates for the Preperation of Sterically Congested Amides and Ketones: A Practical Synthesis of Proscar," *Synthetic Communications*, 30, No. 17, pp. 2683–2690, 1990.

Jones, D.R., et al., "Origin and Structure of Benign Prostatic Hyperplasia," *British Journal of Urology*, 66, pp. 506–508, 1990.

Kutney, J.P. and Johnson, R.A., "Synthesis of 6–Aza–Steroids: A Novel Class of Steroidal Hormones," *Chemistry and Industry*, pp. 1713–1714, Oct. 1961.

Speckamp, W.N., et al., "Synthesis of N–Methyl– and N–Ethyl–6–Aza–8(14)–Dehydroestrone Methyl Ether," *Tetrahedron*, 24, pp. 5881–5891, 1968.

Jacobs, T.L. and Brownfield, R.B., "The Introduction of Oxygen and Nitrogen into the B Ring of the Steroid Nucleus," pp. 4033–4039, Aug. 1960.

Kutney, J.P., et al., "Synthesis of Ring A–Oxygenated 6–Aza Steroids," *Tetrahedron*, 24, pp. 845–857, 1968.

Sampson, W.J., et al, "The Effects of 6–Azacholest–4–en–3b–ol–7–one, an Inhibitor of Cholesterol 7a–Hydroxylase, on Cholesterol Metabolism and Bile Acid Synthesis in Primary Cultures of Rat Hepatocytes," *Biochimica et Biophysica Acta,* 960, pp. 268–274, 1988.

Kutney, J.P., Synthesis of 6–Aza Steroids—A Novel Class of Azaandrostane Analogues, *Canadian J. of Chem.,* 41, pp. 613–619, 1963.

Speckamp, W.N., et al., "Synthesis of N–Methyl–6–Aza–8(14)–Dehydro–19–Nor–Testosterone," *Tetrahedron,* 24, pp. 5893–5898, 1968.

Imperato–McGinley, J., et al., "Androgens and the Evolution of Male–Gender Identity Among Male Pseudohermaphrodites with 5–a Reductase Deficiency," *The New England J. of Med.,* 300, No. 22, pp. 1233–1237, 1979.

Holt, D.A., et al., "Inhibition of Steroid 5a–Reductase by 3–Nitrosteroids: Synthesis, Mechanism of Inhibition, and In Vivo Activity," *Bioorganic & Medicinal Chem. Letters,* 1, No. 1, pp. 27–32, 1991.

Holt, D.A., et al., "Synthesis of a Steroidal A Ring Aromatic Sulfonic Acid as an Inhibitor of Steroid 5a–Reductase," *Steroids,* 56, pp. 4–7, 1991.

Levy, M.A., et al., "Inhibition of Rat Liver Steroid 5a–Reductase by 3–Androstene–3 Carboxylic Acids: Mechanism of Enzyme–Inhibitor Interaction," *Biochemistry,* 29, No. 11, pp. 2815–2824, 1990.

Dupuy, G.M., et al., "Steroidal Inhibitors of Prostatic 5a–Reductase: Structure–Activity Relationships," *Journal of Steroidal Biochemistry,* 9, pp. 1043–1047, 1978.

Metcalf, B.W., "Potent Inhibition of Human Steroid 5a–Reductase (EC 1.3.1.30) by 3–Androstene–3–Carboxylic Acids," *Bioorganic Chemistry,* 17, pp. 372–376, 1989.

Andersson, S., et al., "Deletion of Steroid 5a–Reductase 2 Gene in Male Pseudohermaphroditism," *Nature,* 354, pp. 159–161, 1991.

Thigpen, A.E., et al., "Molecular Genetics of Steroid 5a–Reductase 2 Deficiency," *J. Clin. Invest.,* 90, pp. 799–809, 1992.

Thigpen, A.E., et al., "Brief Report: The Molecular Basis of Steroid 5a–Reductase Deficiency in a Large Dominican Kindred," *New England Jrnl. of Med.,* 327, No. 17, pp. 1216–1219, 1992.

Jenkins, E.P., "Genetic and Pharmacological Evidence for More Than One Human Steroid 5a–Reductase," *J. Clin. Invest.,* 89, pp. 293–300, 1992.

Dave, V., et al., "Resolution of Conflicting Migratory Reports in Ring Expansion of 3–Keto Steroids to Oxygen and Nitrogen," *Canadian J. Chem.,* 58, pp. 2666–2678, 1980.

Kobayashi, M., et al., "Reaction Products of 4–Aza– and 4–Methyl–4–azacholest–5–en–3–one with Nitrous Acid," *Chem. Pharm. Bull.,* 4, No. 20, pp. 789–793, 1972.

Narayanan, C.R., et al., "A Novel Reaction of Nitric Acid with Steroids," *Tetrahedron Letters,* No. 54, pp. 4703–4705, 1970.

Chan, W.K., et al., "The Ihibition of 3βHSD Activity in Porcine Granulosa Cells by 4–MA, a Potent 5α–Reductase Inhibitor," *Biochem. Biophys. Res. Comm.,* 144, No. 1, pp. 166–171, Apr. 14, 1987.

Potts, G.O., et al., "Trilostane, an Orally Active Inhibitor of Steroid Biosynthesis," *Steroids,* 32, No. 2, pp. 257–267, Sep. 1978.

Brandt, M. and Levy, M., "3β–Hydroxy–$\Delta^5$–steroid Dehydrogenase/3–Keto $\Delta^5$–steroid Isomerase from Bovine Adrenals: Mechanism of Inhibition by 3–Oxo–4–aza Steroids and Kinetic Mechanism of the Dehydrogenase," *Biochemistry,* 28, pp. 140–148, 1989.

Bhattacharya, A., et al., "Silylation–Mediated Oxidation of 4–Aza–3–ketosteroids with DDQ Proceeds via DDQ–Substrate Adducts," *J. Am Chem. Soc.,* 110, pp. 3318–3319, 1988.

McConnell, J.D., "Medical Management of Benign Prostatic Hyperplasia with Androgen Suppression," *The Prostate Supplement,* 3, pp. 49–50, 1990.

Diania et al., *Jour Clin Endo & Metab,* 74, 2, pp. 345–350, 1992.

Helliker, *Wall Street Jour,* pp. A1, A7, Jun. 1991.

Stinson, *Chem & Eng. News,* 29, pp. 7–8, Jun. 1992.

ANDROSTENONE DERIVATIVE

This application is a division of application Ser. No. 08,405,120 filed 16 Mar. 1995 which application is now U.S. Pat. No. 5,565,467. This patent application is a continuation-in-part of PCT application No. PCT/US94/10530, filed Sep. 16, 1994 in the name of Glaxo Inc., which is a continuation-in-part of U.S. Ser. No. 08/123,280 filed Sep. 17, 1993 and now abandoned.

The present invention relates to a particular 17β-anilide-4-aza-5α-androst-1-en-3-one derivative, as a surprisingly potent and selective dual inhibitor of type 1 and 2 human 5α-reductase.

BACKGROUND OF THE INVENTION

Androgens are responsible for many physiological functions in both males and females. Androgen action is mediated by specific intracellular hormone receptors expressed in androgen responsive cells. Testosterone, the major circulating androgen, is secreted by Leydig cells of the testes under the stimulation of pituitary-derived luteinizing hormone (LH). However, reduction of the 4, 5 double bond of testosterone to dihydrotestosterone (DHT) is required in some target tissues, such as prostate and skin, for androgen action. Steroid 5α-reductases in target tissues catalyze conversion of testosterone to DHT in an NADPH dependent fashion as shown in Scheme A.

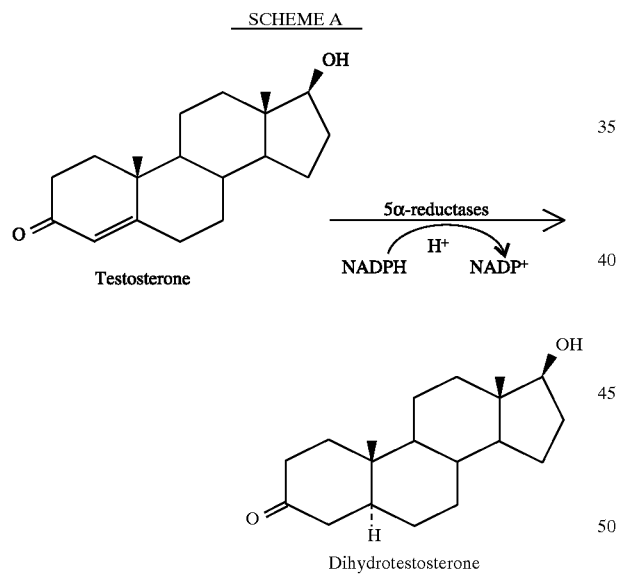

The requirement for DHT to act as an agonist in these target tissues has been highlighted by studies of steroid 5α-reductase deficient individuals who have vestigial prostate glands and do not suffer from acne vulgaris or male pattern baldness (see McGinley, J. et al., *The New England J. of Medicine*, 300, 1233 (1979)). Thus, inhibition of the conversion of testosterone to DHT in these target tissues is anticipated to be useful in the treatment of a variety of androgen responsive diseases, e.g., benign prostatic hyperplasia, prostate cancer, acne, male pattern baldness and hirsutism.

Additionally, it has recently been discovered that two isozymes of 5α-reductase exist in humans which differ in their tissue distribution, affinity for testosterone, pH profile and sensitivity to inhibitors (see Russell, D. W. et al., *J. Clin. Invest.*, 89, 293 (1992); Russell, D. W. et al., *Nature*, 354, 159 (1991)). The steroid 5α-reductase deficient individuals studied by Imperato-McGinley are deficient in the type 2, 5α-reductase enzyme (Russell, D. W. et al., *J. Clin. Invest.*, 90, 799 (1992); Russell, D. W. et al., *New England J. Med.*, 327, 1216 (1992)), which is the predominant isozyme present in the prostate, while the type 1 isozyme is predominant in the skin. The relative value of isozyme specific and dual inhibitors of the two isozymes of 5α-reductase will depend upon the type of disease treated (benign prostatic hyperplasia, prostate cancer, acne, male pattern baldness or hirsutism) as well as the stage of the disease (prevention versus treatment) and the anticipated side-effects in the intended patients (for example treatment of acne vulgaris in pubescent males).

Because of their valuable therapeutic potential, testosterone 5α-reductase inhibitors [hereinafter "5α-reductase inhibitors"] have been the subject of active research worldwide. For example, see: Hsia, S. and Voight, W., *J. Invest. Derm.*, 62, 224 (1973); Robaire, B. et al., *J. Steroid Biochem.*, 8, 307 (1977); Petrow, V. et al., *Steroids*, 38, 121 (1981); Liang, T. et al, *J. Steroid Biochem.*, 19, 385 (1983); Holt, D. et al., *J. Med. Chem.*, 33, 937 (1990); U.S. Pat. No. 4,377,584, U.S. Pat. No. 4,760,071 and U.S. Pat. No. 5,017,568. Two particularly promising 5α-reductase inhibitors are MK-906 (Merck), known by the generic name, finasteride, and marketed under the trademark, Proscar; and SKF-105657 (SmithKline Beecham), shown in Scheme B.

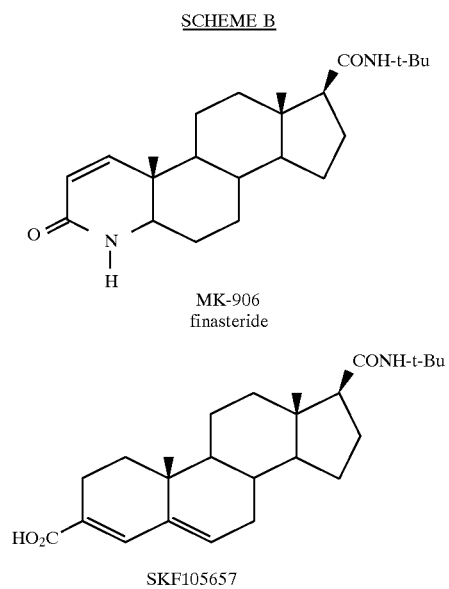

The potent inhibition of bovine adrenal and porcine granulosa cell 3β-hydroxy-Δ⁵-steroid dehydrogenase/3-keto-Δ⁵-steroid isomerase (3BHSD) by the 4-azasteroid derivative, 4-MA, shown in Scheme C and not by the drug finasteride

SCHEME C

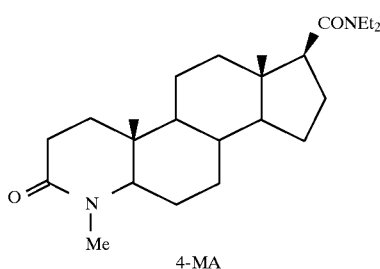

4-MA (Tan, C. H.; Fong, C. Y.; Chan, W. K. *Biochem. Biophys. Res. Comm.*, 144, 166 (1987) and Brandt, M.; Levy, M. A. *Biochemistry*, 28, 140 (1989)), along with the critical role of 3BHSD in steroid biosynthesis (Potts, G. O. et al., *Steroids*, 32, 257 (1978)), suggests that optimal inhibitors of type 1 and 2, 5α-reductase should also be selective versus human adrenal 3BHSD. The importance of selectivity in 5α-reductase inhibitors has been emphasized by reports of hepatotoxicity in certain 4-azasteroids such as 4-MA (McConnell, J. D. *The Prostate Suppl.*, 3, 49 (1990) and Rasmusson, G. H. et al. *J. Med. Chem.*, 27, 1690 (1984)).

SUMMARY OF THE INVENTION

One aspect of the present invention is the compound of formula (I),

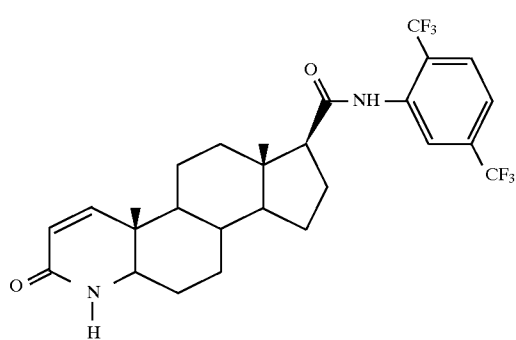

also known as 17β-N-(2,5-bis(Trifluoromethyl))phenylcarbamoyl-4-aza-5α-androst-1-en-3-one and pharmaceutically acceptable salts and solvates thereof.

Other aspects of the invention are:

1. A method of inhibiting testosterone-5α-reductases comprising contacting testosterone-5α-reductases with the compound of formula (I).

2. A method of treatment of androgen responsive or mediated disease comprising administering an effective amount of the compound of formula (I) to a patient in need of such treatment.

3. Pharmaceutical formulations containing the compound of formula (I) as an active ingredient.

4. A method of treatment of androgen responsive or mediated disease comprising administering an effective amount of the compound of formula (I) to a patient in need of such treatment in combination with an anti-androgen such as flutamide.

5. A method of treatment of benign prostatic hyperplasia comprising administering an effective amount of the compound of formula (I) to a patient in need of such treatment in combination with an alpha 1 adrenergic receptor blocker (e.g. terazosin).

6. A method of treatment of benign prostatic hyperplasia comprising administering an effective amount of the compound of formula (I) to a patient in need of such treatment in combination with an anti-estrogen.

7. Intermediates produced in during the synthesis of the compound of formula (I).

DETAILED DESCRIPTION OF THE INVENTION

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of compound (I) are within the scope of the invention.

It will also be appreciated by those skilled in organic chemistry that many organic compounds can exist in more than one crystalline form. For example, crystalline form may vary from solvate to solvate. Thus, all crystalline forms of the compounds of formula (I) or the pharmaceutically acceptable solvates thereof are within the scope of the present invention.

Preparation of Compounds

The compound of the present invention may be prepared by the methods taught in U.S. Pat. Nos. 4,377,584 (hereinafter, "'584") and 4,760,071 (hereinafter, "'071") both incorporated herein by reference. For example, the compound of formula (I) may be prepared by the procedure shown in Scheme I and II.

SCHEME I

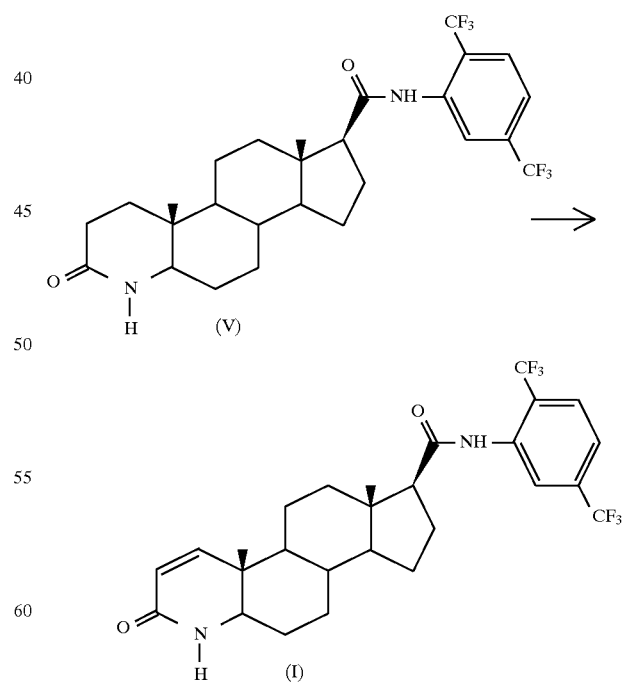

In Scheme I, the compound of formula (V) is dehydrogenated to give the compound of formula (I) by treatment with a dehydrogenating system, e.g. 2,3-dichloro-5,6- dicyano-1,4-benzoquinone (DDQ) and bis(trimethyl-silyl) trifluoroacet-amide in dry dioxane at room temperature for 2–5 hrs followed by heating at reflux for 10–20 hrs (see Bhattacharya, A. et al., *J. Am. Chem. Soc.,* 110,3318 (1988)).

The compound of formula (V) may be prepared according to Scheme IA aprotic solvent such as toluene or methylene chloride to give the amide of formula (III). The compound of formula (IIa) is commercially available (Aldrich Chemical Company, Milwaukee, Wis. 53201).

In Step 2, the compound of formula (III) is converted to the 5-oxo-A-nor-3,5-secoandrostan-3-oic acid derivative of

SCHEME IA

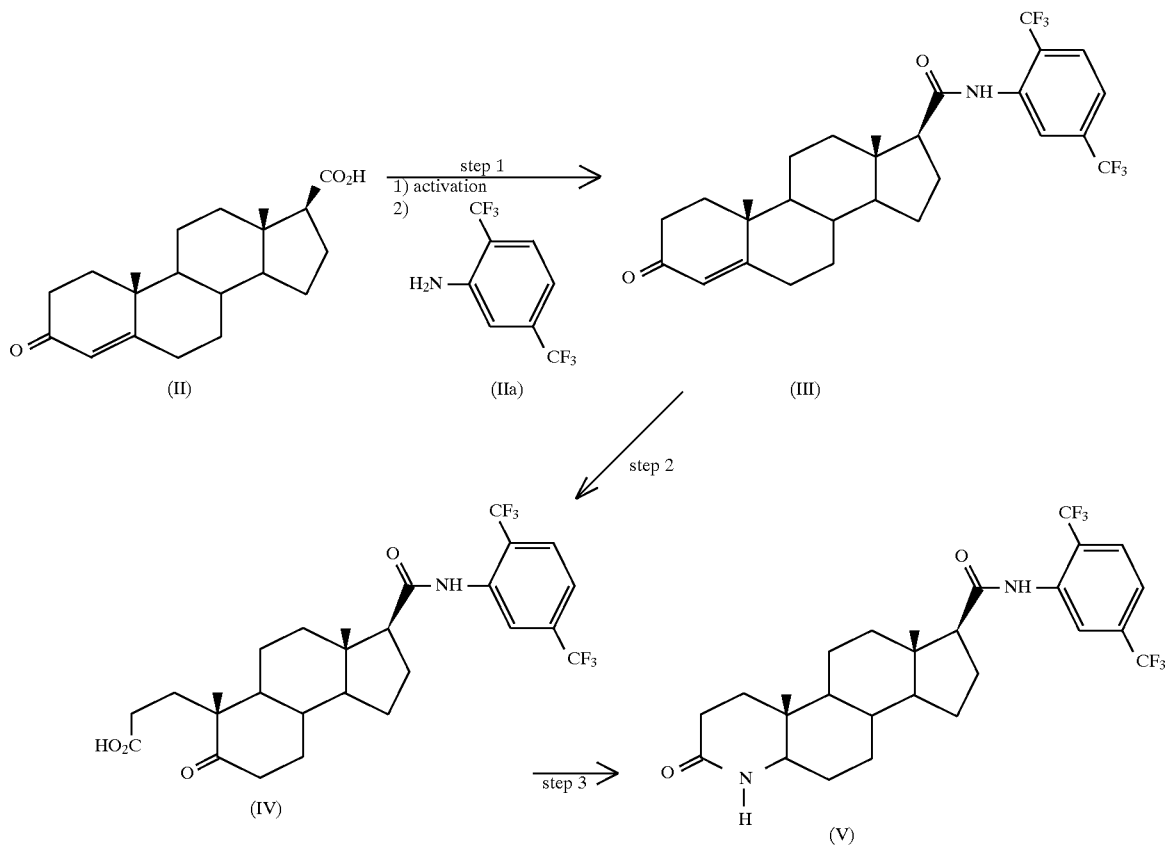

In Step 1 of Scheme IA, 3-oxo-4-androstene-17β-carboxylic acid, (II) is converted to the corresponding amide of formula (III). This may be accomplished by activation of the acid and reaction with an aniline of formula (IIa). For example, the reaction sequence can be the conversion of a compound of formula (II) to the corresponding acid halide by treatment with a halogenating agent such as thionyl chloride or oxalyl chloride in an aprotic solvent such as toluene or methylene chloride at −5° to 10° C. in the presence of a base such as pyridine.

The intermediate acid halide may be reacted with a substituted aniline of formula (IIa) at 25° to 100° C. in an formula (IV) by oxidation, e.g. by treatment with aqueous sodium permanganate and sodium periodate under basic conditions at reflux in t-butanol.

In Step 3, the compound of formula (IV) is converted to the 4-aza-5α-androstan-3-one of formula (V) by treatment with ammonia at reflux in ethylene glycol followed by hydrogenation of the intermediate 4-aza-androst-5-en-3-one in acetic acid at 60° to 70° C. and 40–60 psi hydrogen pressure in the presence of catalytic platinum oxide.

SCHEME II

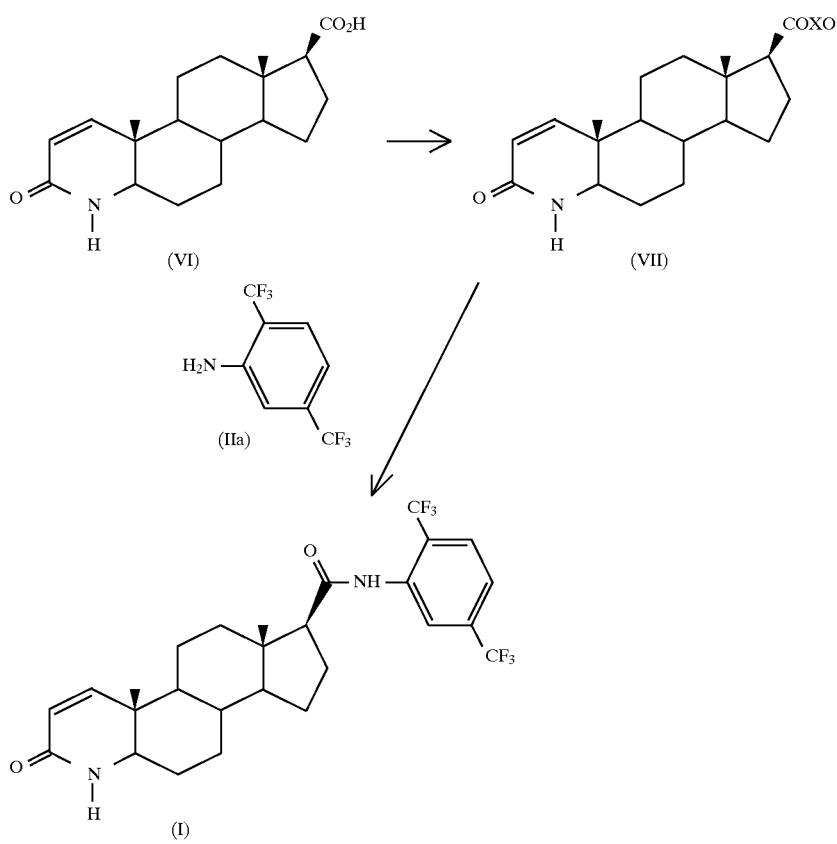

Alternatively, in Scheme II, the compound of formula (I) may be prepared from the 3-oxo-4-aza-5α-androst-1-en-17β-carboxylic acid of formula (VI) (Rasmusson, G. H. et al., *J. Med. Chem.*, 29, 2298 (1986)), through the acid halide intermediate of formula (VII), wherein X is halogen, particularly chloro. The acid chloride of formula (VII) may be produced by treating the corresponding acid of formula (VI) with thionyl chloride in solvents such as toluene, heptane, acetonitrile, triethylphosphate, ethyl acetate, dimethylformamide, N-methypyrrolidinone, dimethylimidazolidinone and dimethyltetrahydropyrimidinone. Persons skilled in the art will realize the addition of a catalytic amount of dimethylformamide can be utilized for acid chloride formation.

The intermediate of formula (VII) wherein X is halogen may be reacted with a substituted aniline of formula (IIa), commercially available (Aldrich Chemical Company, Milwaukee, Wis. 53201, at 25° to 100° C. in an aprotic solvent such as toluene, heptane, acetonitrile, triethylphosphate, ethyl acetate, dimethylformamide, N-methylpyrrolidinone, dimethylimidazolidinone and dimethyltetrahydropyrimidinone to give the compound of formula (I). Bases such as dimethylaminopyridine to assist in the coupling can also be used. Alternative bases such as Diisopropylethylamine, triethylamine and 1,8-diazabicyclo[5.4.0]undec-7-ene might also be used in the preparation of the compound of formula (I). Persons skilled in the art will also realize that the addition of salts such as, LiCl and LiBr, might also be used to facilitate the coupling of the aniline of formula (IIa) with the acid halide of formula (VII) to produce the compound of formula (I).

Those skilled in the art will appreciate that at an earlier stage in the preparation of the compound of formula (I) or a solvate thereof it may have been necessary and/or desirable to protect one or more sensitive groups in the molecule to prevent undesirable side reactions.

The protecting groups used in the preparation of the compound of formula (I) may be used in a conventional manner. See for example Protective Groups in Organic Chemistry, Ed. J. F. W. McOmie, Plenum Press, London (1973) or Protective Groups in Organic Synthesis, Theodora Green, John Wiley and Sons, New York (1981).

Removal of any protecting groups present may be achieved by conventional procedures. An arylalkyl group such as benzyl, may be cleaved by hydrogenolysis in the presence of a catalyst, e.g., palladium on charcoal; an acyl group such as N-benzyloxycarbonyl may be removed by hydrolysis with, for example, hydrogen bromide in acetic acid or by reduction, for example by catalytic hydrogenation.

As will be appreciated, in any of the general processes described above it may be desirable or even necessary to protect any sensitive groups in the molecule as just described. Thus, a reaction step involving deprotection of a protected derivative of general formula (I) or a salt thereof may be carried out subsequent to any of the above described processes.

Thus, according to a further aspect of the invention, the following reactions may, if necessary and/or desired be carried out in any appropriate sequence subsequent to any of the general processes:

(i) removal of any protecting groups; and
(ii) conversion of a compound of formula (I) or a solvate thereof into a pharmaceutically acceptable solvate thereof.

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The compound of formula (I) and the intermediate compounds, (II)–(VI), shown in Schemes I and II may be purified by convenient methods of the art, e.g., chromatography or crystallization.

In Vitro Assays

Steroid 5α-Reductases

Enzyme activies may be determined using microsomes derived from: 1) prostate tissue from benign prostatic hyperplasia (BPH) patients; 2) recombinant baculovirus infected SF9 cells that express human type 1 5α-reductase; or 3) recombinant baculovirus infected SF9 cells that express human type 2 5α-reductase. Microsomes were prepared by homogenization of the tissue or cells, followed by differential centrifugation of the homogenate. Microsome extracts were incubated with varying concentrations of [1,2,6,7-3H]-testosterone, 1 mM NADPH, and varying amounts of the compounds of Formula I, i.e. a test compound, in buffer containing a NADPH regenerating system capable of maintaining NADPH concentrations for a period of time within the range 0.5–240 minutes. Corresponding incubations were carried out with no test compound as a control study. For clone 1 $IC_{50}$ measurements, assay components except testosterone were preincubated for 10 minutes at pH 7.0, and following the addition of 100 nM testosterone the assays were allowed to proceed for 10–120 minutes. For clone 2 $IC_{50}$ measurements, assay components except testosterone were preincubated for 20 minutes at pH 6.0, and following the addition of 8 nM testosterone the assays were allowed to proceed for 20–40 minutes. The percentage of conversion of testosterone to DHT in the presence of test compounds compared to the corresponding conversion in the control study was estimated using high pressure liquid chromatography (HPLC) with radiochemical detection. The results of these assays appear as $IC_{50}$'s reported in Table 1.

3β-Hydroxy-$\Delta^5$-steroid Dehydrogenase/3-Keto-$\Delta^5$-steroid Isomerase Enzyme activities are measured using microsomes derived from human adrenal tissues. Microsomes were prepared by homogenization of the tissue followed by differential centrifugation of the homogenate. Microsome extracts were incubated with varying concentrations of dehydroepiandrosterone (DHEA), 1 mM NAD+, and varying amounts of the compound of Formula (I), i.e. a test compound, in pH 7.5 buffer for a period of time within the range of 1 to 60 minutes. Corresponding incubations were carried out with no test compound as a control study. The percentage of conversion of DHEA to androstenedione in the presence of test compounds compared to the corresponding conversion in the control study was estimated using HPLC with radiochemical detection. The results of these assays appear as $K_i$'s reported in Table 1.

TABLE 1

5α-Reductase (5αR) and Human Adrenal 3β-Hydroxy-$\Delta^5$-Steroid Dehydrogenase/3-Keto-$\Delta^5$-Steroid Isomerase (3βHSD) In Vitro Inhibitory Activity

| $IC_{50}$ Human Type 1 5AR | $IC_{50}$ Human Type 2 5AR | $K_i$ Human Adrenal 3BHSD |
|---|---|---|
| <1nM | <1nM | >1000nM |

In Vivo Evaluation of Steroid 5α-Reductase Inhibitors

The in vivo activity of steroid 5α-reductase inhibitors may be determined in a chronic rat model (Brooks, J. R.. et al., Steroids, 47, 1 (1986)). The chronic model utilizes castrated male rats that are dosed daily with testosterone (20 μg/rat) subcutaneously and with test compound (0.01–10 mg/kg) or vehicle orally for 7 days. The animals are then sacrificed and their prostates weighed. Reduction in the size of testosterone-stimulated prostate weight demonstrated activity of the test compound. Known steroid 5α-reductase inhibitors were tested in parallel to ensure consistency of the assay method.

Utility

The steroid 5α-reductase inhibitor of the present invention is useful in the treatment of androgen responsive diseases, e.g., benign and malignant diseases of the prostate, especially benign prostatic hyperplasia, in a manner similar to that for other 5α-reductase inhibitors such as finasteride and SKF105657. However, the compound of the present invention has a surprisingly long half-life and potency compared to finasteride and SKF105657. For correlation of in vitro, rat in vivo and human clinical data relating to an inhibitor of 5α-reductase, see Stoner, E. et al., J. Steroid Biochem. Molec. Biol., 37, 375 (1990); Brooks, J. R. et al., Steroids, 47, 1 (1986) and Rasmusson, G. H. et al., J. Med. Chem., 29, 2298 (1986)).

The compound of this invention is also useful in the treatment of prostatitis, prostate cancer, androgen mediated diseases of the skin, such as acne, hirsutism and male pattern baldness. Other hormone related diseases, e.g., polycystic ovary disease, may also be treated with this compound.

The amount of the compound of formula (I) required to be effective as an 5α-reductase inhibitor will, of course, vary with the individual mammal being treated and is ultimately at the discretion of the medical or veterinary practitioner. The factors to be considered include the condition being treated, the route of administration, the nature of the formulation, the mammal's body weight, and surface area, age and general condition of the mammal. However, for a human patient a suitable effective 5α-reductase inhibitory dose is in the range of about 0.001 to about 2 mg/kg body weight per day, preferably in the range of about 0.005 to about 1 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 0.04 mg to about 75 mg per day, and a typical dose would be about 10 mg per day. Because of the long half-life of the compound of the present invention, for many patients treatment may only be required every other day, even every third day and possibly less often. If discrete multiple doses are indicated, treatment might typically be 2.5 mg of a compound of formula (I) given 4 times per day.

Formulations

Formulations of the present invention for medical use comprise an active compound, i.e., the compound of formula (I), together with an acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (I) together with a pharmaceutically acceptable carrier thereof.

The formulations include those suitable for oral, topical, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredient(s) may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations suitable for parenteral administration conveniently comprise a sterile aqueous preparation of the active compound which is preferably isotonic with the blood of the recipient. Thus, such formulations may conveniently contain distilled water, 5% dextrose in distilled water or saline and the compound of the formula (I) that has an appropriate solubility in these solvents. Useful formulations also comprise concentrated solutions or solids containing the compound of formula (I) which upon dilution with an appropriate solvent give a solution suitable for parenteral administration above.

Topical formulations include ointments, creams, gels and lotions which may be prepared by conventional methods known in the art of pharmacy. In addition to the ointment, cream gel, or lotion base and the active ingredient, such topical formulation may also contain preservatives, perfumes, and additional active pharmaceutical agents.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The following examples illustrate aspects of this invention but should not be construed as limitations. The symbols and conventions used in these examples are consistent with those used in the contemporary chemical literature, for example, the *Journal of the American Chemical Society*. As used here in the term "room temperature" means about 25° C.

Example 1

17β-N-(2,5-bis(Trifluoromethyl))phenylcarbamoyl-4-aza-5α-androst-1-en-3-one (Synthesis of Scheme I)

A. 17β-N-(2,5-bis(Trifluoromethyl))phenylcarbamoyl-androst-4-en-3-one

To a solution of 3-oxo-4-androstene-17β-carboxylic acid (Rasmusson, G. H. et al., *J. Med. Chem.*, 27, 1690 (1984)) (17.2 g, 54.4 mmol), dry THF (180 mL) and dry pyridine (7 ml) at 2° C. is added thionyl chloride (5.1 mL, 70.8 mmol). The reaction mixture is stirred at 2° C. for 20 min and then stirred at room temperature for 40 min. The reaction mixture is then filtered and the solid washed with toluene. The filtrate is concentrated in vacuo to an oil which is diluted with dry THF (150 mL) and dry pyridine (7 mL). To the resultant dark solution is added 2,5-bis-(trifluoromethyl)aniline (9.4 mL, 59.8 mmol) and the reaction mixture is refluxed for 5 h, diluted with methylene chloride, extracted sequentially with 1N HCl and brine, dried over sodium sulfate, and filtered. The filtrate is concentrated and applied to a column of 500 g of silica gel and the column eluted with a 15–30% ethyl acetate—hexane gradient to give, after concentration, 17β-N-(2,5-bis(trifluoromethyl))phenyl-carbamoyl-androst-4-en-3-one as an off-white foam.

B. 17β-N-(2,5-bis(Trifluoromethyl))phenylcarbamoyl-5-oxo-A-nor-3,5-secoandrostan-3-oic acid To a refluxing solution of 17βN-(2,5-bis(trifluoromethyl)) phenylcarbamoyl-androst-4-en-3-one (18.3 g, 34.9 mmol) prepared as in part A above, t-butanol (275 mL), sodium carbonate (6.3 g, 50.8 mmol), and water (36 mL) is added, over 45 min, a 75° C. solution of potassium permanganate (0.38 g, 2.4 mmol), sodium periodate (52.2 g, 245 mmol) and water (311 mL). After refuxing an additional 15 min, the heterogeneous mixture is cooled to room temperature and celite (50 g) is added. The reaction mixture is filtered through a bed of celite (50 g) and the solid is washed with water and the filtrate concentrated in vacuo to remove t-butanol (ca. 175 ml). The resultant aqueous solution is acidified to pH 2 with 36% HCl and the extracted 4 times with chloroform. The chloroform layers are combined and washed with water, brine, dried over sodium sulfate, filtered and concentrated in vacuo to give 17β-N-(2,5-bis(trifluoromethyl))phenylcarbamoyl-5-oxo-A-nor-3,5-secoandros-tan-3-oic acid as a off-white solid. This material is carried directly into step C below.

C. 17β-N-(2,5-bis(Trifluoromethyl))phenylcarbamoyl-4-aza-androst-5-en-3-one

To a suspension of 17β-N-(2,5-bis(trifluoromethyl))phenylcarbamoyl-5-oxo-A-nor-3,5-secoandrostan-3-oic acid (20.5 g, 34.8 mmol), as prepared in step B, in dry ethylene glycol (100 mL) at room temperature is added ammonia (ca. 8 mL, 0.32 mol) over a 5 min period. The resultant solution is heated to 180° C. over 45 min, and after 12 min at 180° C., the reaction mixture is cooled to 70° C. and water (116 mL) is added over a period of 5 min. The resultant suspension is cooled to 7° C. and stirred for 10 min and filtered under vacuum. The solid is washed with water (60 mL) and then is dissolved in chloroform and washed with water, brine, dried over sodium sulfate, filtered and concentrated. The residue is dissolved in chloroform and applied to a column of 110 g of silica gel and the column eluted with a 2–5% isopropanol-chloroform gradient to give 17β-N-(2,5-bis(trifluoromethyl))phenyl-carbamoyl-4-aza-androst-5-en-3-one as an off-white solid.

D. 17β-N-(2,5-bis(Trifluoromethyl))phenylcarbamoyl-4-aza-5α-androstan-3-one

To a solution of 17β-N-(2,5-bis(trifluoromethyl))phenylcarbamoyl-4-aza-androst-5-en-3-one (8.9 g, 16.7 mmol) in acetic acid (120 mL) is added platinum oxide (0.9 g). The resultant mixture is charged to 50 psi with hydrogen and heated at 60°–70° C. for 6 h. After replacing the hydrogen atmosphere with nitrogen, the reaction mixture is filtered through celite and the celite pad washed with acetic acid (30 mL), chloroform (60 mL) and toluene (200 mL). The filtrate is concentrated in vacuo to an oil, toluene (200 mL) is added and the solution concentrated to a foam in vacuo. The foam is crystallized from ethyl acetate-heptane to give, after drying in vacuo at 85° C. for 1 h, 17β-N-(2, 5-bis(trifluoromethyl))phenylcarbamoyl-4-aza-5α-androstan-3-one; m.p. 245°–247° C. Anal. Calcd. for $C_{27}H_{32}F_6N_2O_2$: C, 61.12; H, 6.08; N, 5.28. Found: C, 61.13; H, 6.12; N, 5.21.

E. 17β-N-(2,5-bis(Trifluoromethyl))phenylcarbamoyl-4-aza-5α-androstan-1-en-3-one To a suspension of 17β-N-(2,5-bis(Trifluoromethyl))phenylcarbamoyl-4-aza-5α-androstan-3-one (7.24 g, 13.7 mmol) and 2,3-dichloro-5,6-dicyano-1,4-benzoquinone (3.41 g, 15 mmol) in dry dioxane (168 mL) at room temperature is added bis(trimethylsilyl)trifluoroacetamide (14.5 mL, 54.6 mmol). After stirring at room temperature for 7 h, the reaction mixture is refluxed for 18 h. The resultant dark solution is cooled to room temperature and is concentrated in vacuo to a dark oil. Methylene chloride (100 mL) and a 1% sodium bisulfite solution (40 mL) is added to the oil and the two phase mixture is stirred rapidly for 15 min and filtered. The two filtrate layers are separated and the methylene chloride layer is washed sequentially with 2N HCl and brine, dried over sodium sulfate, filtered, and concentrated to a brown oil. The oil is diluted with toluene and is applied to a column of 300 g of silica gel and eluted with a 12:3:1 to 9:3:1 gradient of toluene:acetone:ethyl acetate to give 17β-N-(2,5-bis(trifluoromethyl))phenyl-carbamoyl-4-aza-5α-androst-1-en-3-one as a foam. This material is crystallized from ethyl acetate-heptane (1:1) to give a white solid; m.p. 244°–245° C. $^{13}$C NMR (100 MHz, CHCl$_3$) d 171.31, 166.77, 151.04, 136.35 (q, J=1.4 Hz), 135.01 (q, J=33.1 Hz), 126.73 (q, J=5.4 Hz), 123.44 (q, J=273.5 Hz), 123.03 (q, J=273.2 Hz), 122.84, 121.58 (qq, J=30.4, 1.0 Hz), 120.37 (q, J=3.6 Hz), 120.29 (q, J=3.9 Hz), 59.58, 58.33, 55.69, 47.46, 44.78, 39.30, 37.81, 35.29, 29.34, 25.70, 24.17, 23.59, 21.15, 13.40, 11.91.

Anal. Calcd. for $C_{27}H_{30}F_6N_2O_2$: C, 61.36; H, 5.72; N, 5.30. Found: C, 61.36; H, 5.73; N, 5.23.

Example 2

17β-N-(2, 5-bis(Trifluoromethyl))phenylcarbamoyl-4-aza-5α-androst-1-en-3-one (Synthesis of Scheme II)

A solution of 3-oxo-4-aza-5α-androst-1-en-17β-carboxylic acid (31.7 g, 100 mmol) in pyridine (800 mL) is cooled to −10° C., and thionyl chloride (14.3 g, 120 mol) is added with stirring. The mixture is allowed to stir 2.5–3 hours at 20° C., to form the acid chloride (17β-chlorocarbonyl-4-aza-5α-androst-1-en-3-one); IR 1780 cm$^{-1}$, FAB-MS [MH]$^+$=336.

To the stirring acid chloride 2,5-bis(trifluoromethyl) aniline (23.1 g, 101 mol) is added. Stirring is continued for 4–6 hours, 960 mL of water is added and the slurry is stirred at room temperature overnight. Filtration gives the crude product as an off-white solid. The crude solid is recrystallized by dissolution in 725 mL of acetonitrile at 70° C. and removal of acetonitrile by distillation gives, after cooling and filtration, 17β-N-2,5-bis(Trifluoromethyl) phenylcarbamoyl-4-aza-5α-androst-1-en-3-one as a white crystalline solid.

Example 3

Pharmaceutical Formulations

"Active compound" is the compound of Formula (I)

| (A) Transdermal System - For 1000 Patches | |
|---|---|
| Ingredients | Amount |
| Active compound | 40 g |
| Silicone fluid | 450 g |
| Colloidal silicon dioxide | 25 g |

The silicone fluid and active compound are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 sq. cm patches.

(B) Oral Tablet - For 1000 Tablets

| Ingredients | Amount |
| --- | --- |
| Active compound | 20 g |
| Starch | 20 g |
| Magnesium Stearate | 1 g |

The active compound and the starch are granulated with water and dried. Magnesium stearate is added to the dried granules and the mixture is thoroughly blended. The blended mixture is compressed into tablets.

(C) Suppository - For 1000 Suppositories

| Ingredients | Amount |
| --- | --- |
| Active compound | 25 g |
| Theobromine sodium salicylate | 250 g |
| Witepsol S55 | 1725 g |

The inactive ingredients are mixed and melted. The active compound is then distributed in the molten mixture, poured into molds and allowed to cool.

(D) Injection - For 1000 Ampules

| Ingredients | Amount |
| --- | --- |
| Active Compound | 5 g |
| Buffering Agents | q.s. |
| Propylene glycol | 400 mg |
| Water for injection | 600 mL |

The active compound and buffering agents are dissolved in the propylene glycol at about 50° C. The water for injection is then added with stirring and the resulting solution is filtered, filled into ampules, sealed and sterilized by autoclaving.

(E) Capsule - For 1000 Capsules

| Ingredients | Amount |
| --- | --- |
| Active Compound | 20 g |
| Lactose | 450 g |
| Magnesium stearate | 5 g |

The finely ground active compound is mixed with the lactose and stearate and packed into gelatin capsules.

What is claimed is:

1. A method of treating an androgen responsive or mediate condition in a mammal suffering from said condition comprising administering to said mammal a safe and effective amount of 17β-N-(2,5-bis(Trifluoromethyl)) phenylcarbamoyl-4-aza-5α-androst-1-en-3-one or a pharmaceutically acceptable solvate thereof.

2. A method of claim 1 wherein the androgen responsive or mediated condition is benign prostatic hypertrophy, prostate cancer, acne, male pattern baldness and hirsutism.

3. A method of treating an androgen responsive or mediated condition in a mammal suffering from said condition comprising administering to said mammal a safe and effective amount of a pharmaceutical formulation comprising a safe and effective amount of 17β-N-(2,5-bis(Trifluoromethyl)) phenylcarbamoyl-4-aza-5α-androst-1-en-3-one or a pharmaceutically acceptable solvate thereof.

4. The method of claim 3 wherein said formulation further comprises an alpha 1 adrengergic receptor blocker.

5. The method of claim 3 wherein said formulation further comprises an anti-estrogen selected from the group consisting of: clomiphene and tamoxifen.

6. The method of claim 5 wherein said anti-estrogen is tamoxifen.

7. The method of claim 3 wherein said formulation further comprises an anti-androgen.

8. The method of claim 6 wherein said anti-androgen is flutamide.

* * * * *

UNITED STATES PATENT AND TRADEMARK OFFICE
CERTIFICATE OF CORRECTION

PATENT NO. : 5,846,976
DATED : December 8, 1998
INVENTOR(S) : Batchelor, et al.

It is certified that error appears in the above-indentified patent and that said Letters Patent is hereby corrected as shown below:

Column 16, Claim 2, line 3, change "and" to --,or--.

Signed and Sealed this

Sixteenth Day of November, 1999

Attest:

Q. TODD DICKINSON

*Attesting Officer*  *Acting Commissioner of Patents and Trademarks*

UNITED STATES PATENT AND TRADEMARK OFFICE
Certificate

Patent No. 5,846,976                                          Patented: December 8, 1998

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Robert A. Mook, Jr.; George F. Dorsey; Kenneth W. Batchelor; and Stephen V. Frye.

Signed and Sealed this First Day of February, 2000.

MARIANNE CINTINS
*Supervisory Patent Examiner*
Technology Center 1600
Art Unit 1614

UNITED STATES PATENT AND TRADEMARK OFFICE
CERTIFICATE OF CORRECTION

PATENT NO. : 5,846,976
DATED : December 8, 1998
INVENTOR(S) : Batchelor et al.

It is certified that error appears in the above-identified patent and that said Letters Patent is hereby corrected as shown below:

On petition requesting issuance of a certificate of correction of inventorship under 35 U.S.C. § 256, the above-indentified patent, through error and without deceptive intent, improperly sets forth inventorship.

Accordingly, the correct inventorship of this patent is: Kenneth W. Batchelor and Stephen V. Frye.

Signed and Sealed this

Nineteenth Day of March, 2002

*Attest:*

JAMES E. ROGAN
*Director of the United States Patent and Trademark Office*

*Attesting Officer*